(12) United States Patent
Nakayama et al.

(10) Patent No.: US 7,400,707 B2
(45) Date of Patent: Jul. 15, 2008

(54) APPARATUS FOR AND METHOD OF CAPTURING RADIATION IMAGE

(75) Inventors: Hiroki Nakayama, Aiko-gun (JP); Tomonari Sendai, Minami-ashigara (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 11/704,944

(22) Filed: Feb. 12, 2007

(65) Prior Publication Data

US 2007/0201617 A1 Aug. 30, 2007

(30) Foreign Application Priority Data

Feb. 24, 2006 (JP) ............................. 2006-048519
Nov. 28, 2006 (JP) ............................. 2006-319962

(51) Int. Cl.
*H05G 1/44* (2006.01)
*H05G 1/42* (2006.01)
*A61B 6/04* (2006.01)

(52) U.S. Cl. ............................. 378/108; 378/37; 378/97

(58) Field of Classification Search .................... 378/37, 378/108–117, 62, 64, 65, 97, 162, 165
See application file for complete search history.

(56) References Cited

U.S. PATENT DOCUMENTS

| 5,619,042 | A | * | 4/1997 | Hughes | 250/492.3 |
|---|---|---|---|---|---|
| 5,867,555 | A | * | 2/1999 | Popescu et al. | 378/16 |
| 5,949,811 | A | * | 9/1999 | Baba et al. | 378/108 |
| 6,233,310 | B1 | * | 5/2001 | Relihan et al. | 378/108 |
| 6,249,565 | B1 | * | 6/2001 | Tarr | 378/65 |
| 6,577,709 | B2 | * | 6/2003 | Tarr | 378/108 |
| 2003/0133534 | A1 | * | 7/2003 | Bothe et al. | 378/16 |

FOREIGN PATENT DOCUMENTS

| JP | 05-087607 | 4/1993 |
|---|---|---|
| JP | 05-299955 A | 11/1993 |
| JP | 3052969 B2 | 4/2000 |
| JP | 2004-298383 A | 10/2004 |

* cited by examiner

*Primary Examiner*—Irakli Kiknadze
(74) *Attorney, Agent, or Firm*—Sughrue Mion, PLLC

(57) ABSTRACT

Before a radiation image is captured, a rate of change of an output signal from an integrator, during a given period of time after the integrator has been reset and until a radiation start signal is supplied, is calculated. An offset voltage signal at a desired time is calculated using the rate of change, and is supplied to a voltage correcting circuit. An output signal from the integrator after a radiation X has started being applied to a subject is corrected based on the calculated offset voltage signal. The corrected output signal from the integrator is supplied to an X-ray tube controller for controlling application of the radiation X to the subject.

19 Claims, 8 Drawing Sheets

APPARATUS FOR AND METHOD OF CAPTURING RADIATION IMAGE

BACKGROUND OF THE INVENTION

1. Field of the Invention

The present invention relates to an apparatus for and a method of capturing a radiation image by emitting radiation from a radiation source and applying the emitted radiation to a subject, and for controlling the radiation source based on the dose of radiation applied to the subject.

2. Description of the Related Art

In the medical field, for example, it has been customary to apply radiation to a subject and to detect the amount of radiation that has passed through the subject with a radiation detector, or to guide the radiation that has passed through the subject directly to an X-ray film or the like, thereby forming a radiation image of the subject for diagnostic purposes.

For obtaining a radiation image suitable for image interpretation and diagnosis, a tube voltage, a tube current, and a radiation application time are established as appropriate exposure conditions, depending on the body region to be imaged and other characteristics of the radiation source. There is known an image capturing system with an automatic exposure control function, which controls the dose of radiation to be applied to a subject, by detecting the dose of radiation that has passed through the subject with a dose detector, and then automatically stopping application of radiation when the detected dose reaches a predetermined value (see Japanese Laid-Open Patent Publication No. 2004-298383).

In the image capturing system having such an automatic exposure control function, a small current output from the dose detector is converted into a voltage signal by a current-to-voltage converter. The voltage signal is amplified at a high magnification by an amplifier, and the amplified voltage signal is integrated with respect to time by an integrator, thereby determining a radiation dosage.

However, since the radiation dosage is determined after a low voltage signal has been amplified at a high magnification, the image capturing system having such an automatic exposure control function is problematic in that a temperature-dependent characteristic change of the circuit components tends to cause a large error in the determined radiation dosage.

In order to compensate for such temperature-dependent characteristic changes of the circuit components, there has widely been employed a process of canceling out the characteristic circuit component changes using a temperature compensating device, whose input/output characteristics change depending on temperature, such as a thermistor, a diode, or the like, wherein the temperature compensating device is inserted into the system circuitry (see Japanese Laid-Open Patent Publication No. 5-87607 and Japanese Laid-Open Patent Publication No. No. 5-299955).

The temperature characteristics of the temperature compensating device vary from unit to unit. Therefore, if the temperature compensating device is not thermally coupled adequately to the circuit component whose temperature-dependent characteristic change is to be compensated for, then the temperature compensating device cannot provide highly accurate temperature compensation. In addition, the circuit component has its own time-variable characteristics, and as a practical matter, it is difficult to select a temperature compensating device that is capable of handling variations in characteristics.

SUMMARY OF THE INVENTION

It is a general object of the present invention to provide an apparatus for and a method of capturing a radiation image while highly accurately determining the radiation dosage, so as to control a radiation source regardless of temperature-dependent and time-dependent characteristic changes in the circuit components thereof.

A major object of the present invention is to provide an apparatus for and a method of capturing a radiation image by applying an appropriate radiation dosage to a subject regardless of temperature-dependent and time-dependent characteristic changes in the circuit components thereof.

With the apparatus for and method of capturing a radiation image according to the present invention, before radiation is applied to a subject to capture a radiation image of the subject, a rate of change of an output value provided from a radiation dosage calculating unit is determined. An offset value, for correcting the output value of the radiation dosage calculating unit, is determined using the rate of change. A radiation dosage calculated by the radiation dosage calculating unit, or a preset required radiation dosage, is corrected based on the offset value, in order to appropriately control the radiation source so as to capture a radiation image, regardless of characteristic changes in the circuit components.

The above and other objects, features, and advantages of the present invention will become more apparent from the following description when taken in conjunction with the accompanying drawings in which preferred embodiments of the present invention are shown by way of illustrative example.

DESCRIPTION OF THE PREFERRED EMBODIMENTS

Figure 1:
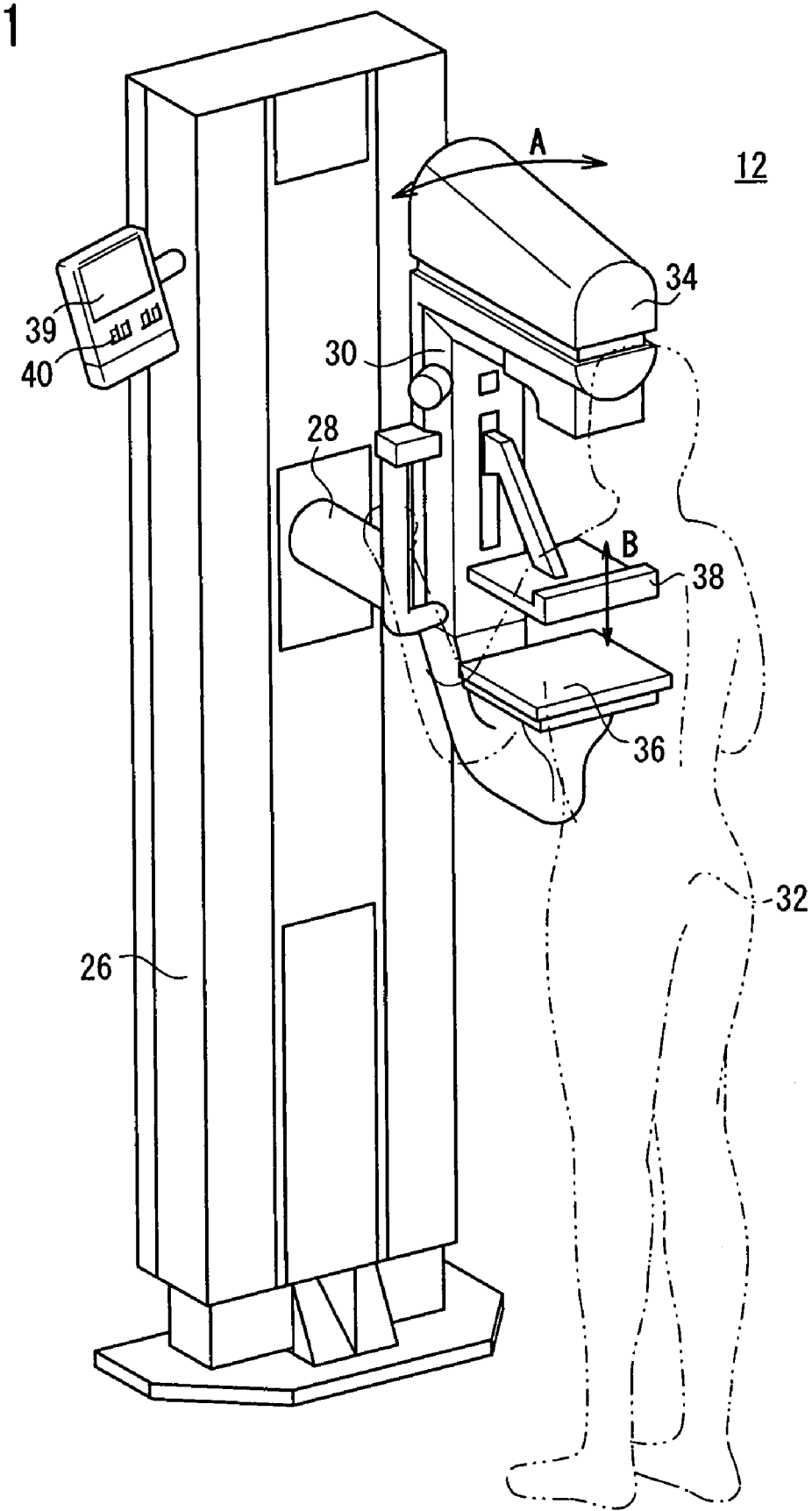
FIG. 1 is a perspective view of a mammographic system according to an embodiment of the present invention.

FIG. 1 shows in perspective a mammographic system 12 to which an apparatus for and method of capturing a radiation image according to an embodiment of the present invention are applied.

As shown in FIG. 1, the mammographic system 12 has an upstanding base 26, a vertical arm 30 fixed to a horizontal swing shaft 28 disposed substantially centrally on the base 26, a radiation source housing unit 34 storing a radiation source for applying radiation to a subject 32 and which is fixed to an upper end of the arm 30, an image capturing base 36 housing a solid-state detector for detecting radiation that has passed through the subject 32 and which is fixed to a lower end of the arm 30, and a presser plate 38 for pressing and holding the subject's breast against the image capturing base 36.

When the arm 30, to which the radiation source housing unit 34 and the image capturing base 36 are secured, is angularly moved about the swing shaft 28 in a direction indicated by the arrow A, an image capturing direction with respect to the breast of the subject 32 can be adjusted. The presser plate 38 is connected to the arm 30 and is disposed between the radiation source housing unit 34 and the image capturing base 36. The presser plate 38 is vertically displaceable along the arm 30 in a direction indicated by the arrow B.

To the base 26, there are connected a control panel 40 for entering image capturing information including ID information of the subject 32, an image capturing region of the subject 32, a tube voltage, a target type, the type of filter to be mounted in an opening 58 (see FIG. 2) for adjusting the radiation dose, etc., and a display panel 39 for displaying the entered image capturing information.

The display panel 39 and the control panel 40 may be mounted on a console (not shown) connected to the mammographic system 12, rather than being mounted on the mammographic system 12 itself.

Figure 2:
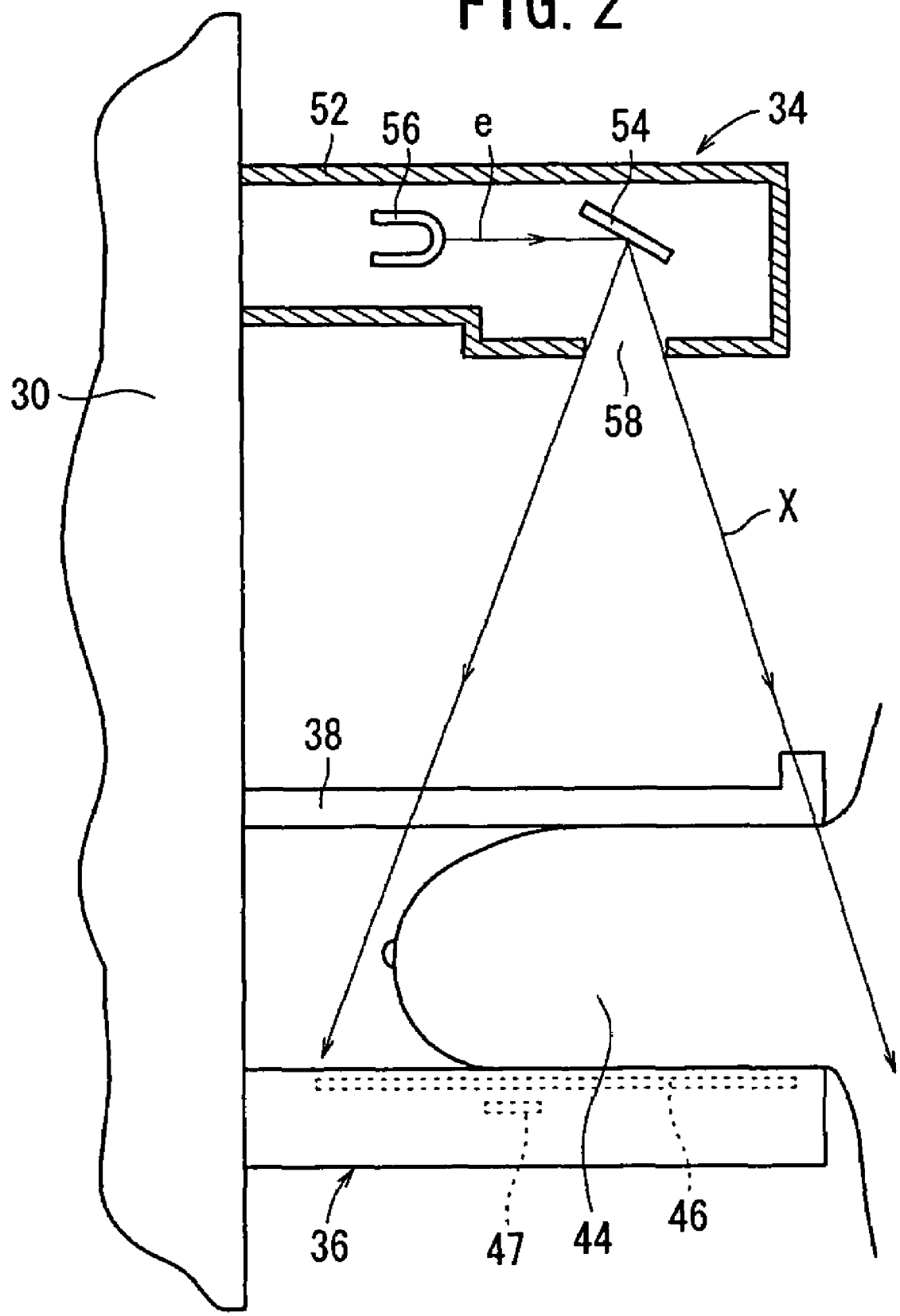
FIG. 2 is a fragmentary vertical elevational view, partly in cross section, showing internal structural details of a radiation source housing unit of the mammographic system according to the embodiment of the present invention.

FIG. 2 shows internal structural details of the radiation source housing unit 34.

As shown in FIG. 2, the radiation source housing unit 34 has a target 54 serving as a radiation source made of molybdenum, tungsten, or the like, which is placed in a housing 52, and a cathode 56 for emitting an electron beam "e" to the target 54. The housing 52 has an opening 58 defined in a lower wall thereof through which radiation X, which is generated when the electron beam "e" emitted from the cathode 56 bombards the target 54, passes toward a breast 44 of the subject 32 that is to be imaged within a predetermined exposure field. The housing 52 is made of a heavy metal for preventing radiation from leaking outside of the housing 52.

Figure 3:
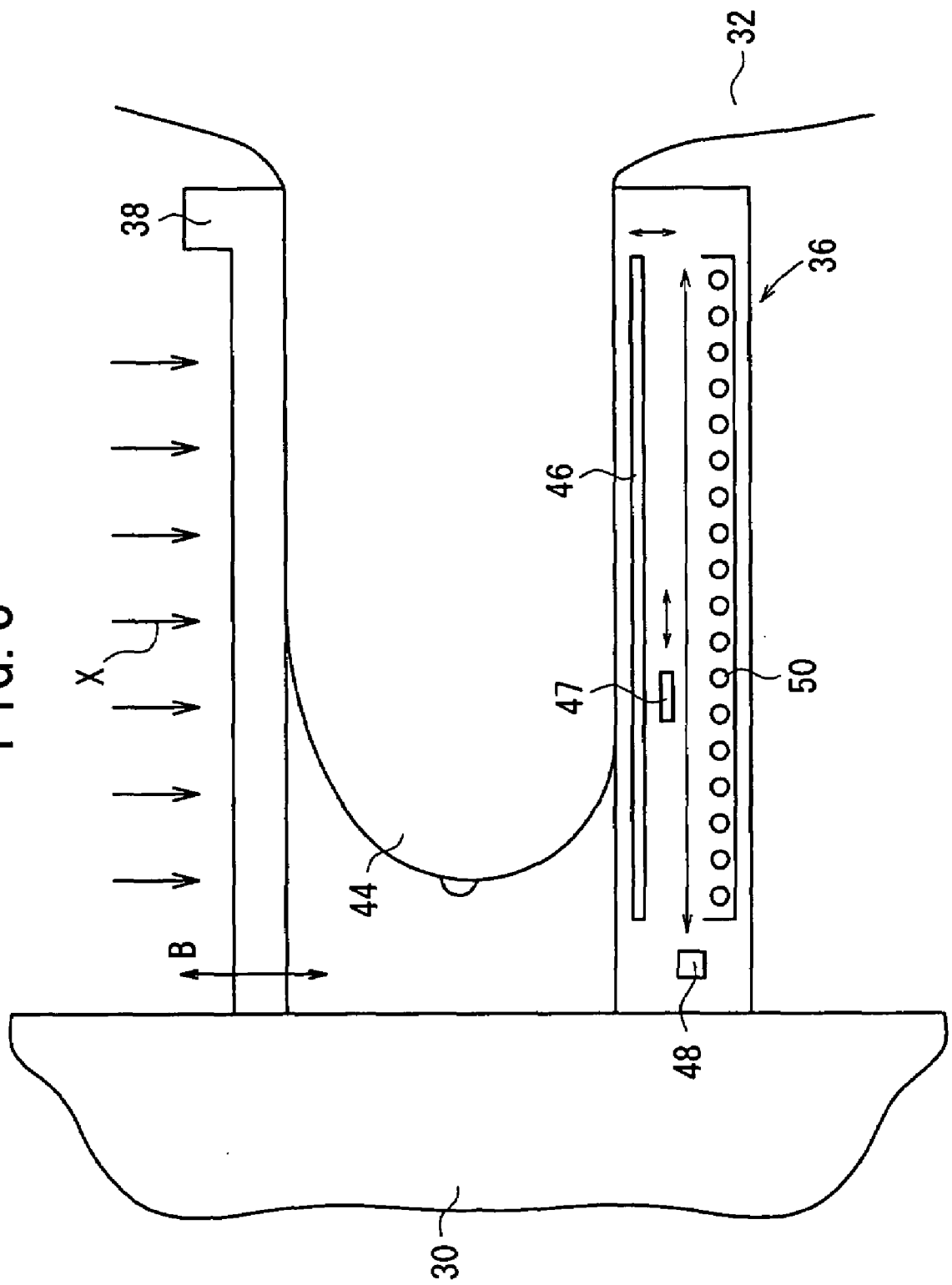
FIG. 3 is a fragmentary vertical elevational view, partly in cross section, showing internal structural details of an image capturing base of the mammographic system according to the embodiment of the present invention.

FIG. 3 shows internal structural details of the image capturing base 36 of the mammographic system 12. In FIG. 3, the breast 44 of the subject 32 is shown as being placed between the image capturing base 36 and the presser plate 38.

The image capturing base 36 houses therein an X-ray detector 46 for detecting the radiation X that is emitted from the target 54 of the radiation source housing unit 34 through the opening 58, an exposure control sensor 47 (dose detecting means) for detecting the dose of radiation X that has passed through a desired region of the breast 44 for performing exposure control, a reading light source 48 for applying a reading light to the X-ray detector 46 so as to read information of the radiation X that is detected by the X-ray detector 46, and an erasing light source 50 for applying an erasing light to the X-ray detector 46 in order to remove unwanted electric charges accumulated within the X-ray detector 46.

The X-ray detector 46 comprises a direct-conversion light-reading radiation solid-state detector. The X-ray detector 46 stores information of the radiation X that has passed through the breast 44 as an electrostatic image, and when the X-ray detector 46 is scanned by reading light applied from the reading light source 48, generates a current depending on the electrostatic image.

More specifically, the X-ray detector 46 comprises a laminated assembly made up of a first electrically conductive layer disposed on a glass substrate for passing the radiation X therethrough, a recording photoconductive layer for generating electric charges upon exposure to the radiation X, a charge transport layer which acts substantially as an electric insulator with respect to latent image polarity electric charges developed in the first electrically conductive layer, and further which acts substantially as an electric conductor with respect to transport polarity charges, which are of a polarity opposite to the latent image polarity electric charges, a reading photoconductive layer for generating electric charges and which becomes electrically conductive upon exposure to the reading light, and a second electrically conductive layer which is permeable to the radiation X. An electric energy storage region is provided within an interface between the recording photoconductive layer and the charge transport layer.

The first electrically conductive layer and the second electrically conductive layer each provides an electrode. The electrode provided by the first electrically conductive layer comprises a two-dimensional flat electrode. The electrode provided by the second electrically conductive layer comprises a plurality of linear electrodes, which are spaced at a predetermined pixel pitch, for detecting the information of the radiation X that is to be recorded as an image signal. The linear electrodes are arranged in an array along a main scanning direction, and extend in an auxiliary scanning direction perpendicular to the main scanning direction.

The reading light source 48 has, for example, a line light source comprising a linear array of LED chips and an optical system for applying a line of reading light emitted from the line light source to the X-ray detector 46. The linear array of LED chips extends perpendicularly to the direction in which the linear electrodes of the second electrically conductive layer of the X-ray detector 46 extend. The line light source moves along the direction in which the linear electrodes extend so as to expose and scan the entire surface of the X-ray detector 46.

The erasing light source 50 should preferably comprise a light source, which can emit and quench light within a short period of time and which has very short persistence. For example, the erasing light source 50 may comprise a plurality of external-electrode rare-gas fluorescent lamps, extending along the direction of the array of LED chips of the reading light source 48, and arranged in an array perpendicular to the direction of the array of LED chips of the reading light source 48.

The exposure control sensor 47 comprises a photodiode or the like, which is movable to a desired position between the X-ray detector 46 and the erasing light source 50, for detecting the dose of radiation X that has passed through the desired region of the breast 44. The desired region of the breast 44 may be the mammary gland region, for example.

Figure 4:
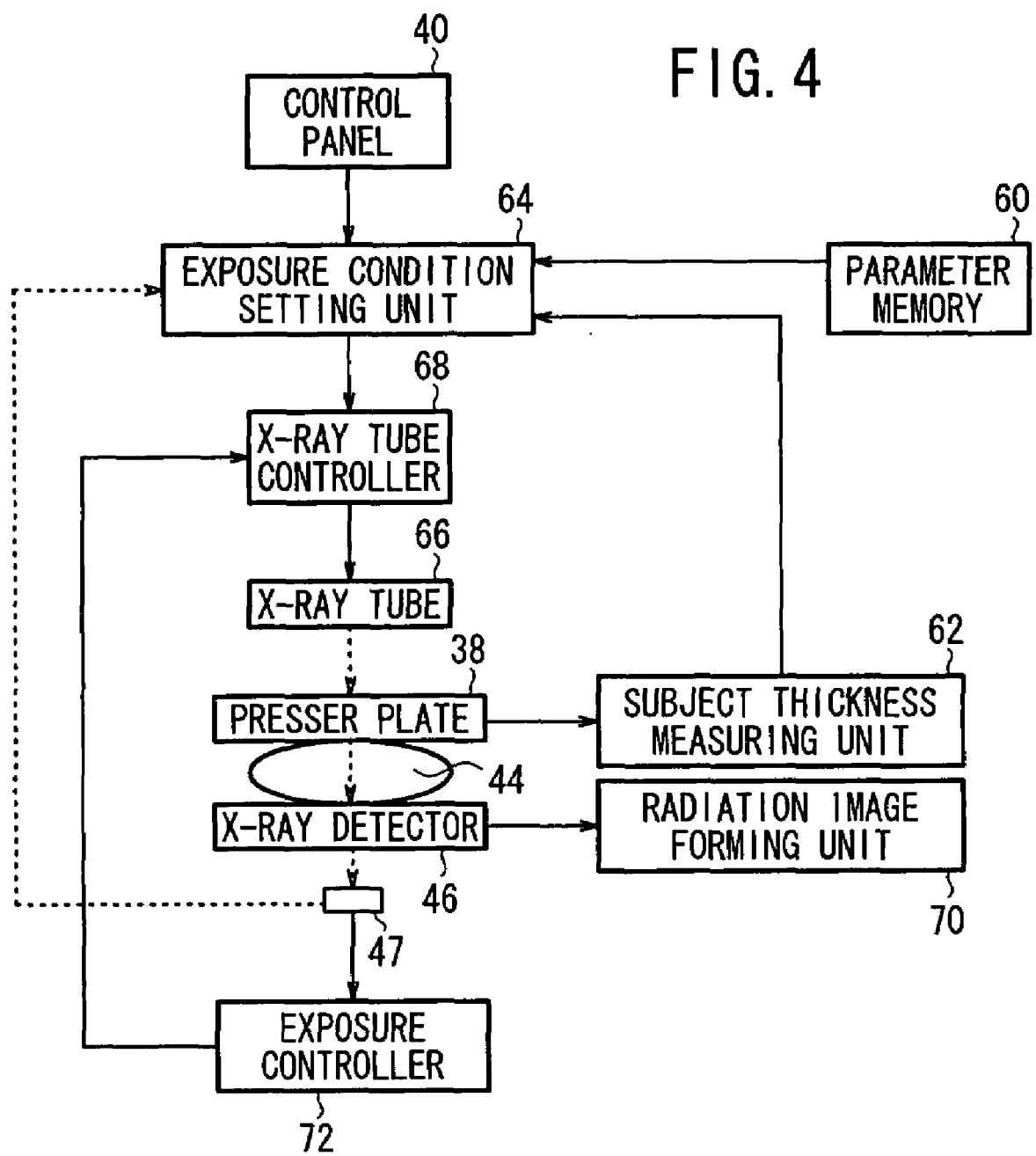
FIG. 4 is a block diagram of a control circuit of the mammographic system according to the embodiment of the present invention.

FIG. 4 shows in block form a control circuit of the mammographic system 12.

As shown in FIG. 4, the mammographic system 12 includes a parameter memory 60 for storing various parameters such as the absorption rates of different regions to be imaged at which the subject 32 absorbs the radiation X, the absorption rate at which the presser plate 38 absorbs the radiation X, the sensitivity of the X-ray detector 46, an index that depends on the atomic number of the target 54, the attenuation characteristics of the radiation X depending on the distance between the target 54 and the X-ray detector 46, etc. The mammographic system 12 further includes a subject thickness measuring unit 62 for measuring from positional information of the presser plate 38 a subject thickness, i.e., the thickness of a region to be imaged, and an exposure condition setting unit 64 for setting exposure conditions including a tube current, a radiation application time, a radiation dosage, etc., using image capturing information representing the region to be imaged of the subject 32, a tube voltage, the target 54 and the filter types that have been entered from the control panel 40, parameters read from the parameter memory 60, and data of the subject thickness supplied from the subject thickness measuring unit 62. In addition, the mammographic system 12 includes an X-ray tube controller 68 for controlling an X-ray tube 66, which comprises the cathode 56 and the target 54 of the radiation source housing unit 34, according to exposure conditions set by the exposure condition setting unit 64, a radiation image forming unit 70 for forming a radiation image of the breast 44 based on information of the radiation X detected by the X-ray detector 46, and an exposure controller 72 for calculating a radiation dosage applied to a desired region of the breast 44 from the dose of radiation X detected by the exposure control sensor 47, and controlling the X-ray tube controller 68 so as to automatically stop application of radiation X to the breast 44 when the calculated radiation dosage reaches a predetermined value set as an exposure condition. The X-ray tube controller 68 and the exposure controller 72 jointly serve as a radiation source control means.

Figure 5:
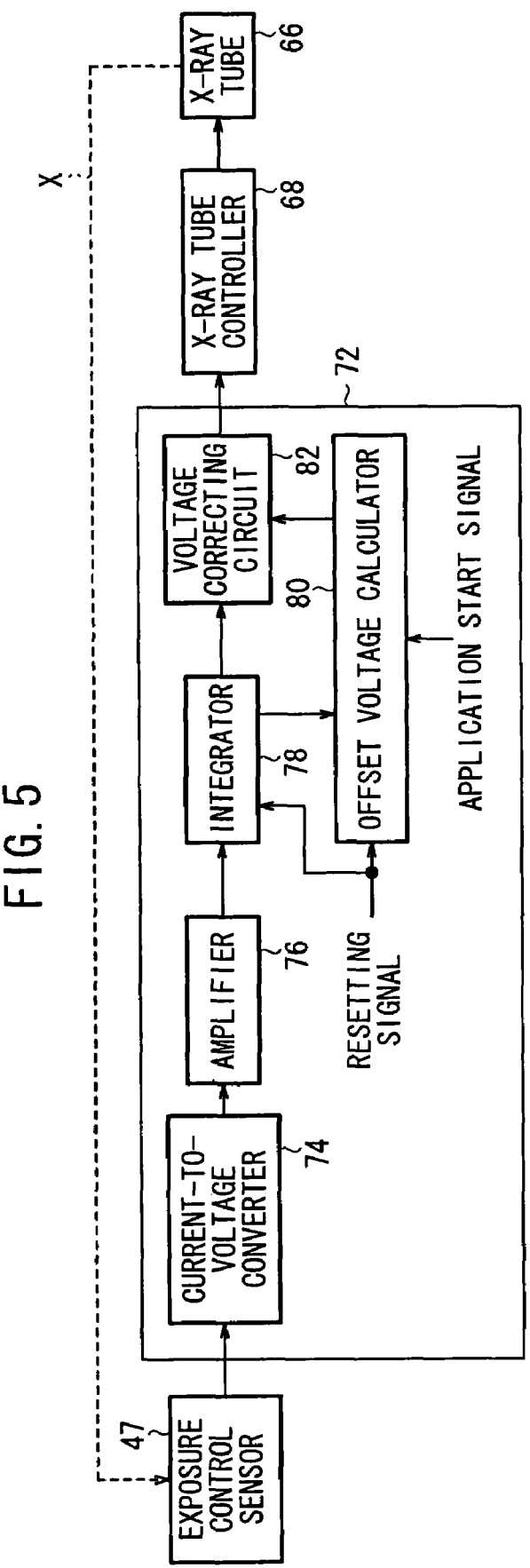
FIG. 5 is a block diagram of an exposure controller of the control circuit shown in FIG. 4.

FIG. 5 shows the exposure controller 72 in block form.

As shown in FIG. 5, the exposure controller 72 comprises a current-to-voltage converter 74 for converting a current signal representative of the dose of radiation X detected by the exposure control sensor 47 into a voltage signal, an amplifier 76 for amplifying the voltage signal at a high magnification, an integrator 78 (radiation dosage calculating means) for integrating the amplified voltage signal with respect to time in order to calculate a voltage signal representing a radiation dosage based on the radiation X. The exposure controller 72 further comprises an offset voltage calculator 80 for calculating an offset voltage signal representing an offset value for compensating temperature-dependent and time-dependent changes in the outputs from the circuit components, including the exposure control sensor 47, the current-to-voltage converter 74, the amplifier 76, the integrator 78, etc., based on a time-integrated voltage signal output from the integrator 78. Finally, the exposure controller 72 includes a voltage correcting circuit 82 (radiation dosage correcting means) for correcting the voltage signal output from the integrator 78 using the offset voltage signal supplied from the offset voltage calculator 80.

The offset voltage calculator 80 is supplied with a resetting signal for resetting the integrator 78, and an application start signal for energizing the X-ray tube 66 to begin applying radiation X to the subject 32. During a period of time after the offset voltage calculator 80 is supplied with the resetting signal and until it is supplied with the application start signal, the offset voltage calculator 80 functions as a rate-of-change calculating means for calculating a rate of change of the voltage signal output from the integrator 78. During this period, the offset voltage calculator 80 also functions as an offset value calculating means for calculating an offset voltage signal representing an offset value from the calculated rate of change.

The mammographic system 12 according to the present embodiment is basically constructed as described above. Operations of the mammographic system 12 shall be described below.

Using the control panel 40 attached to the mammographic system 12, the non-illustrated console, and/or an ID card, etc., the operator enters image capturing information including ID information of the subject 32, an image capturing direction, an image capturing region, the tube voltage to be applied to the X-ray tube 66, the type of the target 54 of the X-ray tube 66, the type of the filter for dosage adjustment, etc. In the description that follows, it shall be assumed that the operator is capable of setting image capturing information using the control panel 40 and of confirming the image capturing information displayed on the display panel 39.

Having entered the image capturing information, the operator places the mammographic system 12 into a certain state according to the specified image capturing direction. For example, the breast 44 may be imaged as a cranio-caudal view (CC) taken from above, a medio-lateral view (ML) taken outwardly from the center of the chest, or a medio-lateral oblique view (MLO) taken from an oblique view. Depending on the selected information of one of these image capturing directions, the operator turns the arm 30 about the swing shaft 28.

Then, the operator places the subject into a specified image capturing state with respect to the mammographic system 12. For example, if the breast 44 of the subject 32 is to be imaged as a cranio-caudal view (CC), the operator places the subject's breast 44 onto the image capturing base 36, and thereafter lowers the presser plate 38 to hold the breast 44 in place between the image capturing base 36 and the presser plate 38, as shown in FIG. 3.

After the breast 44 has been placed in a desired image capturing state, the subject thickness measuring unit 62 measures a subject thickness, i.e., the thickness of the breast 44, and supplies the measured data to the exposure condition setting unit 64.

Using information of the region to be imaged of the subject 32, the tube voltage, the type of target 54, and the type of filter, which have been entered from the control panel 40, the parameters read from the parameter memory 60, which include the absorption rate of the region to be imaged where the region to be imaged absorbs the radiation X, the absorption rate at which the presser plate 38 absorbs the radiation X, the sensitivity of the X-ray detector 46, an index depending on the atomic number of the target 54, the attenuation characteristics of the radiation X depending on the distance between the target 54 and the X-ray detector 46, and the subject thickness supplied from the subject thickness measuring unit 62, the exposure condition setting unit 64 calculates a tube current to be supplied to the X-ray tube 66 along with a radiation application time, calculates the dosage of the radiation X that is required to capture a radiation image of the region to be imaged, and sets the calculated values as exposure conditions in the X-ray tube controller 68.

For example, assuming the energy of the radiation X to be applied to the X-ray detector 46 is represented by E, the energy E is expressed by:

$$E = K \cdot V^n \cdot I \cdot t \cdot S/L^2 \cdot \exp(-\mu \cdot d) \tag{1}$$

where K represents a characteristic value peculiar to the mammographic system 12, V is the tube voltage, n is a tube voltage index, t is the application time of the radiation X, S is the sensitivity of the X-ray detector 46, L is the distance between the target 54 and the X-ray detector 46, μ is the absorption rate at which the region to be imaged absorbs the radiation X, and d is the subject thickness. If the energy E (radiation dosage) required in order for the X-ray detector 46 to be able to detect the radiation X is given highly accurately, then the exposure conditions of the tube current I and the radiation application time t, which ate required to capture the radiation image, can be established according to the above equation (1), using the parameters including the subject thickness d.

After the exposure conditions have been established in the manner described above, the exposure control sensor 47 is moved in the direction indicated by the arrow in FIG. 3 to a position aligned with the mammary gland region of the breast 44, for example. Then, a radiation image of the breast 44 starts being captured. Before the X-ray tube controller 68 energizes the X-ray tube 66 to apply the radiation X to the breast 44, the X-ray tube controller 68 supplies resetting signals to the integrator 78 and to the offset voltage calculator 80 of the exposure controller 72, in order to reset the voltage signal output from the integrator 78 to 0 V, and also to reset the offset voltage signal calculated by the offset voltage calculator 80 to 0 V. Then, the X-ray tube controller 68 is supplied with an application start signal.

After the X-ray tube controller 68 is supplied with the application start signal, the X-ray tube controller 68 applies the tube voltage entered from the control panel 40 to the X-ray tube 66, and energizes the X-ray tube 66 according to the exposure conditions, including the tube current and the radiation application time set by the exposure condition setting unit 64. When the tube voltage is applied between the cathode 56 and the target 54 of the X-ray tube 66, and the tube current set as the exposure condition flows therebetween, the cathode 56 emits an electron beam "e". When the emitted electron beam "e" bombards the target 54, the target 54 emits radiation X. The radiation X emitted from the target 54 passes through the opening 58 and is applied through the presser plate 38 to the breast 44. The radiation X passes through the breast 44 and is applied to the X-ray detector 46, which is housed in the image capturing base 36. Before a radiation image is captured, the entire surface of the X-ray detector 46 is irradiated with erasing light from the erasing light source 50 in order to remove unwanted electric charges from the X-ray detector 46.

After the radiation X has passed through the breast 44, the radiation X carries radiation image information of the breast 44. When the radiation X, which carries the radiation image information of the breast 44, is applied to the X-ray detector 46 while a high voltage is applied between the first electrically conductive layer and the second electrically conductive layer, pairs of positive and negative electric charges are generated in the recording photoconductive layer of the X-ray detector 46. The negative electric charges are stored in the electric energy storage region that is provided in the interface between the recording photoconductive layer and the charge transport layer. The amount of stored negative electric charge, i.e., the amount of latent image polarity electric charge, is substantially proportional to the dose of radiation X that has passed through the breast 44. The positive electric charges generated within the recording photoconductive layer are attracted to the first electrically conductive layer, where they are combined with the negative electric charges of the applied high voltage and hence are eliminated.

The dose of radiation X applied to the breast 44 is detected by the exposure control sensor 47 and supplied to the exposure controller 72. The exposure controller 72 calculates a radiation dosage applied to the desired region of the breast 44 on the basis of the detected dose of radiation X, and supplies the calculated radiation dosage back to the X-ray tube controller 68 through a feedback loop. When the radiation dosage supplied from the exposure controller 72 to the X-ray tube controller 68 reaches the set radiation dosage, which is set as an exposure condition, the X-ray tube controller 68 outputs an application termination signal in order to stop supplying the tube current to the X-ray tube 66. As a result, the radiation image capturing cycle is finished.

Operation of the exposure controller 72 shall be described in detail below.

Figure 6:
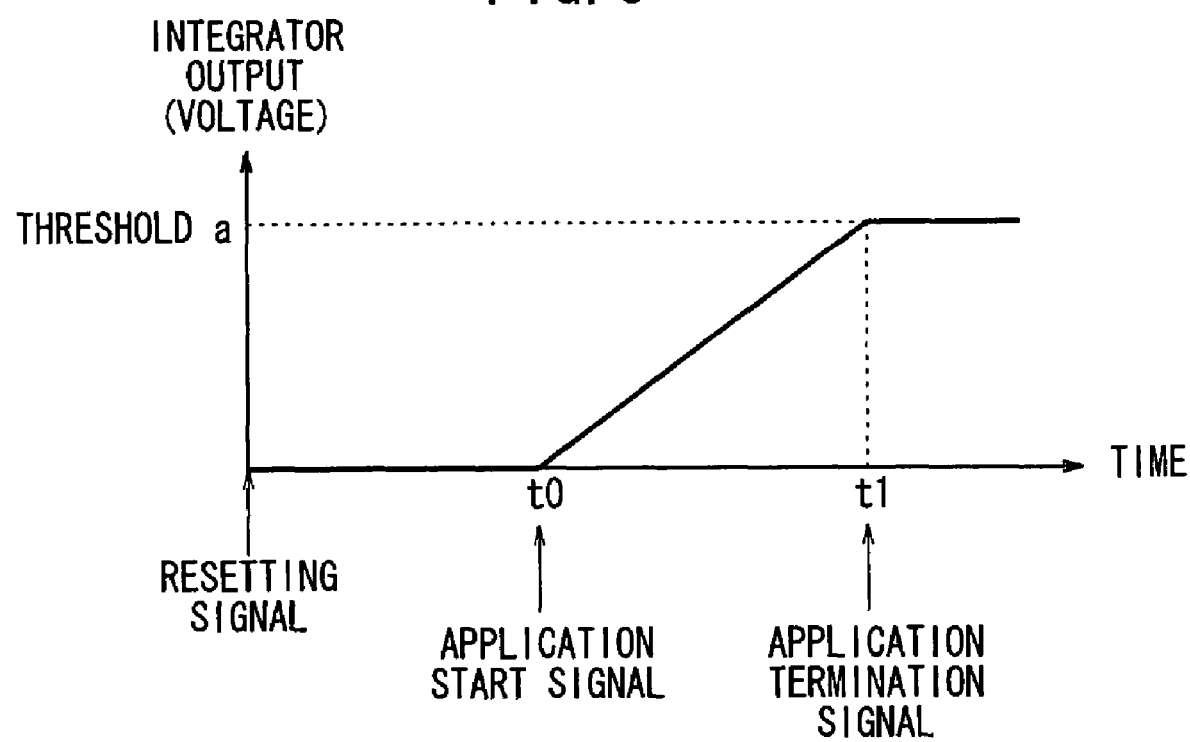
FIG. 6 is a diagram showing an output signal from an integrator, in an ideal condition wherein the circuit components are not affected by temperature.

Assuming that signals output from the circuit components of the exposure control sensor 47 and the exposure controller 72 are ideal and do not depend on temperature, then the time-integrated voltage signal output from the integrator 78 has a waveform as shown in FIG. 6.

Specifically, if the voltage signal output from the integrator 78 is not affected by temperature after the integrator 78 has been supplied with the resetting signal and until the X-ray tube controller 68 is supplied with the application start signal, then the voltage signal output from the integrator 78 remains at 0 V. Then, the application start signal is supplied to the X-ray tube controller 68 to energize the X-ray tube 66, which applies the radiation X to the exposure control sensor 47. The exposure control sensor 47 detects the dose of radiation X. The exposure control sensor 47 supplies a current signal representative of the detected dose of radiation X to the current-to-voltage converter 74, which converts the current signal into a voltage signal. The voltage signal output from the current-to-voltage converter 74 is amplified by the amplifier 76, and the amplified voltage signal is supplied to the integrator 78. The integrator 78 integrates the supplied voltage signal with respect to time, and supplies a voltage signal representative of the radiation dosage to the X-ray tube controller 68. The X-ray tube controller 68 compares the voltage signal supplied from the integrator 78 with a threshold value "a", which represents a predetermined radiation dosage set as an exposure condition. When the voltage signal agrees with the threshold value "a" at time t1, the X-ray tube controller 68 outputs an application termination signal to the X-ray tube 66, which then stops application of the radiation X.

The above operation is based on the assumption that signals output from the circuit components are ideal. Usually, however, signals which are output from the circuit components of the exposure control sensor 47 and the exposure controller 72 tend to vary due to temperature changes and other time-dependent characteristic changes. According to the present embodiment, the voltage signal output from the integrator 78 is corrected for temperature compensation by the offset voltage calculator 80 and the voltage correcting circuit 82.

Figure 7:
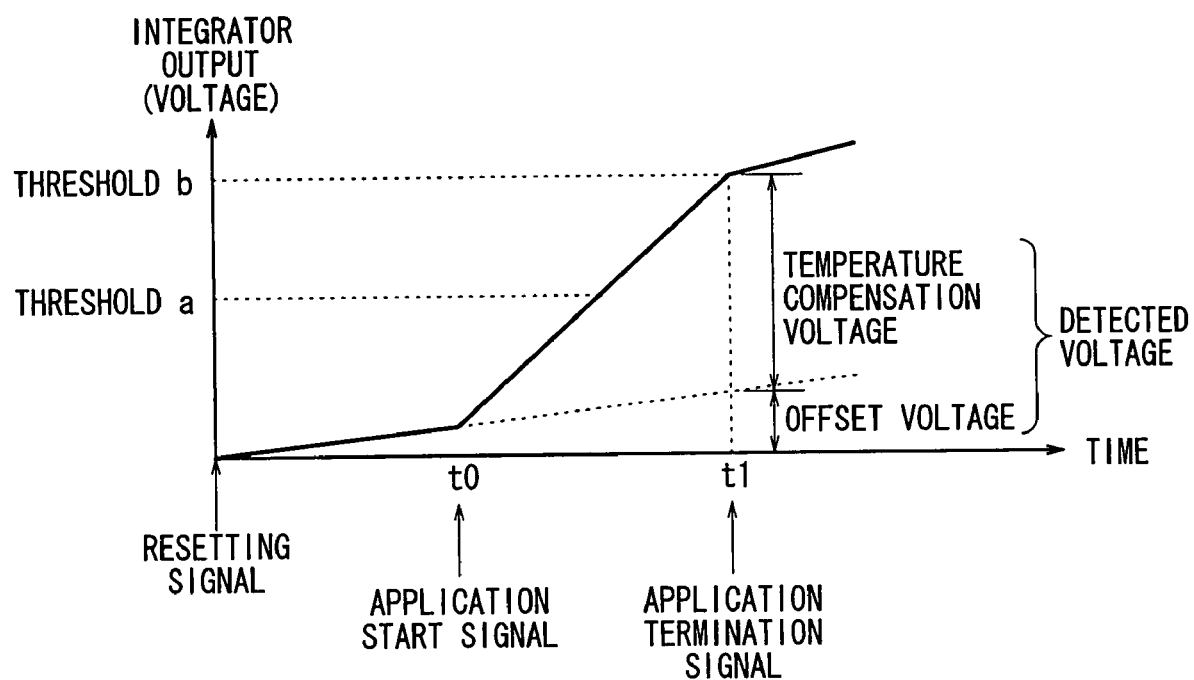
FIG. 7 is a diagram showing an output signal from the integrator, in a condition wherein the circuit components are affected by temperature.

During the period of time after the offset voltage calculator 80 is supplied with the resetting signal and until the offset voltage calculator 80 is supplied with the application start signal, the offset voltage calculator 80 calculates a rate of change of the voltage signal output from the integrator 78. FIG. 7 shows the time-integrated voltage signal output from the integrator 78.

Since the exposure control sensor 47 and the circuit components, including the current-to-voltage converter 74, the amplifier 76, etc., of the exposure controller 72 are susceptible to ambient temperature, the integrator 78 outputs a voltage signal that progressively increases after the integrator 78 is supplied with the resetting signal and until the X-ray tube controller 68 is supplied with the application start signal. Assuming that such temperature changes of the exposure controller 72, during the short period of time after the resetting signal is supplied and until the application start signal is supplied, can be ignored and the output signal from the integrator 78 during this period can be approximated by a linear function, then the rate of change a of the voltage signal, which depends on ambient temperature and characteristics of the circuit components, can be calculated on the basis of the time t0 when the application start signal is input after the resetting signal has been input, and the voltage signal output from the integrator 78 at time t0.

The offset voltage calculator 80 calculates an offset voltage signal Voff as follows, using the calculated rate of change α and the time t from the supply of the resetting signal:

$$\text{Voff} = \alpha \cdot t \quad (2)$$

Then, when the application start signal is supplied to the X-ray tube controller 68 to energize the X-ray tube 66 that applies the radiation X to the exposure control sensor 47, the exposure control sensor 47 detects the dose of radiation X, and then supplies a voltage signal representing the dose of radiation X to the voltage correcting circuit 82 through the current-to-voltage converter 74, the amplifier 76, and the integrator 78. The voltage correcting circuit 82 subtracts the offset voltage signal Voff, which is determined by the equation (2), from the voltage signal, and then outputs a temperature compensation voltage signal, which has been corrected using the offset voltage signal Voff, to the X-ray tube controller 68.

The X-ray tube controller 68 then compares the temperature compensation voltage signal from the voltage correcting circuit 82 with the threshold value "a". When the temperature compensation voltage signal agrees with the threshold value "a" at time t1, the X-ray tube controller 68 outputs an application termination signal to the X-ray tube 66, which stops application of the radiation X. At this time, the offset voltage signal Voff is expressed as Voff=α·t1.

In the present embodiment, since the offset voltage signal is calculated from the rate of change of the output signal from the integrator 78, during a period of time after the resetting signal is supplied and until the application start signal is supplied, and since the output signal from the integrator 78 is corrected using the offset voltage signal, signals output from the circuit components of the exposure control sensor 47, etc., can be temperature-compensated easily with high accuracy. As a result, the radiation dosage of the desired region of the breast 44 exposed to the radiation X is highly accurately controlled for capturing an appropriate radiation image of the region. The offset voltage signal may be calculated in each radiation image capturing cycle, in order to control an optimum radiation dosage depending on the ambient temperature of the mammographic system 12 at the time the radiation image is captured.

Figure 8:
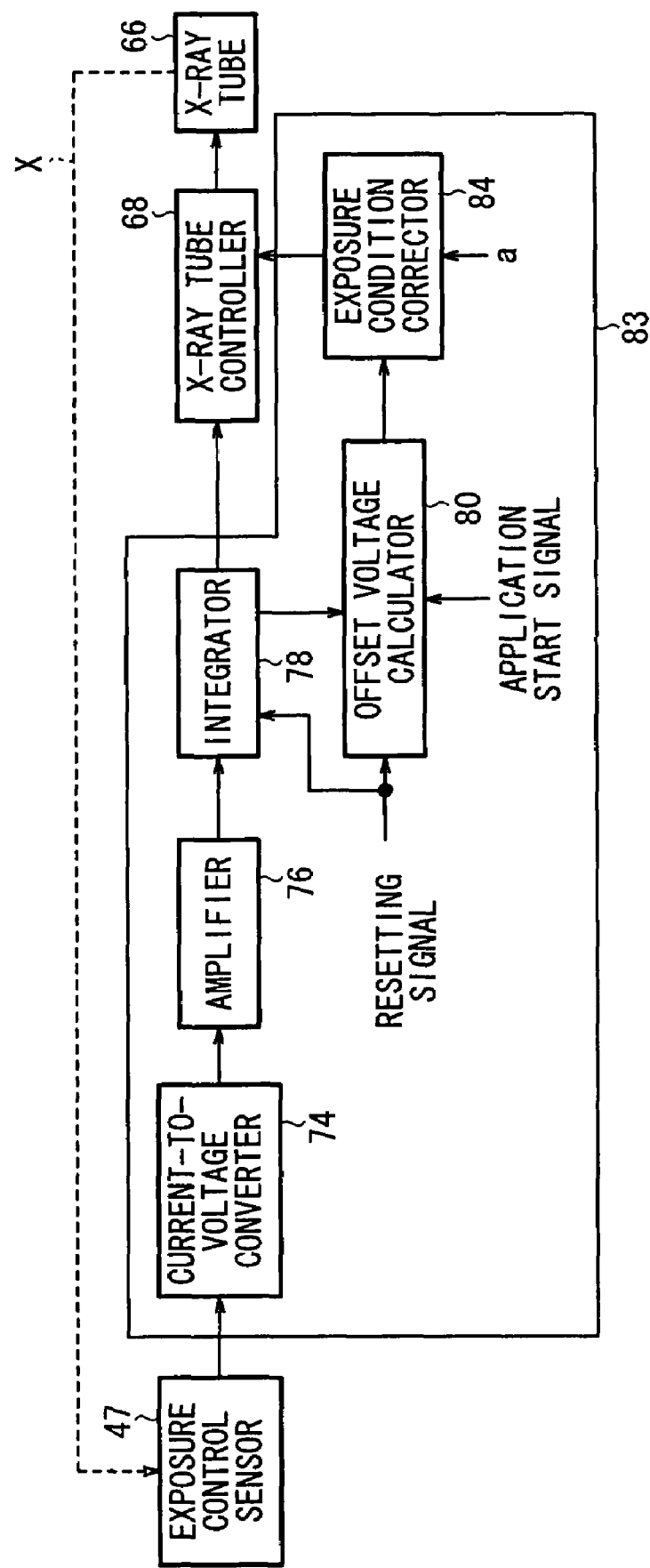
FIG. 8 is a block diagram of an exposure controller according to another embodiment of the present invention.

In the above embodiment, the voltage signal output from the integrator 78 is corrected by the offset voltage signal in the voltage correcting circuit 82, and the corrected voltage signal is supplied to the X-ray tube controller 68. FIG. 8 shows in block form an exposure controller 83 according to another embodiment of the present invention. In the exposure controller 83, the voltage signal output from the integrator 78 is not corrected, but rather, is supplied to the X-ray tube controller 68, and the offset voltage signal calculated by the offset voltage calculator 80 is supplied to an exposure condition corrector 84 (required radiation dosage correcting means). The exposure condition corrector 84 adds the offset voltage signal to the threshold "a" representing a required radiation dosage set as the exposure condition, thereby setting a new threshold "b" representative of a new required radiation dosage. Then, the X-ray tube controller 68 compares the voltage signal output from the integrator 78 with the threshold "b" for controlling the radiation dosage.

After the application termination signal is supplied to the X-ray tube 66 to terminate the image capturing cycle, the exposure control sensor 47 is retracted from the position between the X-ray detector 46 and the erasing light source 50. Then, the reading light source 48 moves in the direction indicated by the arrow along the X-ray detector 46 while applying the reading light to the X-ray detector 46. In the X-ray detector 46, pairs of positive and negative electric charges are generated within the reading photoconductive layer, and the positive electric charges are attracted to the negative electric charges (latent image polarity electric charges) stored in the electric energy storage region and move within the charge transport layer. The positive electric charges then combine with the negative electric charges in the electric energy storage region and are eliminated. The negative electric charges generated within the reading photoconductive layer are combined with the negative electric charges supplied to the second photoelectric conductive layer and are eliminated. In this manner, the negative electric charges stored in the X-ray detector 46 are eliminated by charge combination, whereupon a current is developed within the X-ray detector 46 due to movement of the electric charges for performing charge combination. The current developed within the X-ray detector 46 is supplied to the radiation image forming unit 70, which produces a radiation image of the breast 44 based on the supplied current. After the radiation image has been formed, the X-ray detector 46 is irradiated with erasing light emitted from the erasing light source 50 in order to remove unwanted electric charges accumulated within the X-ray detector 46, and thereby preparing the X-ray detector 46 for the next radiation image capturing cycle.

In the above embodiments, as described above, exposure conditions are established based on various parameters stored in the parameter memory 60, and on information representative of the thickness of the breast 44 as measured by the subject thickness measuring unit 62, wherein a radiation image is captured according to the exposure conditions thus established.

The principles of the present invention are also applicable to an image capturing system in which a "pre-exposure" mode is first performed in order to apply a small prescribed dose of the radiation X to the breast 44, and then exposure conditions are established based on the dose of the radiation X that has passed through the breast 44. Thereafter, a "main exposure" mode is performed so as to apply the radiation X to the breast 44 according to the established exposure conditions, for thereby capturing a desired radiation image of the breast 44.

Specifically, after the breast 44 has been positioned on the image capturing base 36, a small prescribed dose of the radiation X is applied from the X-ray tube 66 to the breast 44 in the "pre-exposure" mode, and then the dose of radiation X that has passed through the breast 44 is detected by the exposure control sensor 47. The dose of radiation X that is detected by the exposure control sensor 47 is supplied to the exposure condition setting unit 64, as indicated by the dotted lines in FIG. 4, and the exposure condition setting unit 64 establishes the exposure conditions. After the "pre-exposure" mode, a resetting signal is supplied to the integrator 78 and to the offset voltage calculator 80. The offset voltage calculator 80 calculates a rate of change of the voltage signal output from the integrator 78 during a period of time after the offset voltage calculator 80 has been supplied with the resetting signal and until it is supplied with the application start signal for starting the "main exposure" mode. In the "main exposure" mode, an application start signal is supplied to the X-ray tube controller 68 so as to energize the X-ray tube 66, which applies the radiation X to the breast 44 according to the exposure conditions established during the "pre-exposure" mode. During the "main exposure" mode, the X-ray tube 66 is controlled based on a radiation dosage, which is corrected based on the rate of change of the voltage signal that has been calculated between the "pre-exposure" mode and the "main exposure" mode.

Although certain preferred embodiments of the present invention have been shown and described in detail, it should be understood that various changes and modifications may be made to the embodiments without departing from the scope of the invention set forth in the appended claims.

What is claimed is:

1. An apparatus for capturing a radiation image by emitting radiation from a radiation source and applying the radiation to a subject to capture a radiation image thereof, and for controlling said radiation source based on a radiation dosage applied to the subject, comprising:
    dose detecting means for detecting a dose of said radiation applied to said subject;
    radiation dosage calculating means for integrating the detected dose of said radiation with respect to time to calculate a radiation dosage applied to the subject;
    rate-of-change calculating means for calculating a rate of change of a time-integrated output signal from said radiation dosage calculating means before said radiation image is captured by applying said radiation to said subject;
    offset value calculating means for calculating an offset value of said radiation dosage from said rate of change;
    dosage correcting means for correcting said radiation dosage calculated by said radiation dosage calculating means based on said offset value; and
    radiation source control means for controlling said radiation source based on said radiation dosage corrected by said dosage correcting means.

2. An apparatus according to claim 1, wherein said rate-of-change calculating means calculates said rate of change before said radiation is applied.

3. An apparatus according to claim 1, wherein said rate-of-change calculating means calculates said rate of change before said radiation is applied to capture said radiation image and after said radiation is applied to said subject to establish exposure conditions for said radiation source.

4. An apparatus according to claim 1, wherein said rate-of-change calculating means calculates said rate of change dependent on a temperature of said radiation image capturing apparatus.

5. An apparatus according to claim 1, wherein said rate-of-change calculating means calculates said offset value Voff as:

$$Voff = \alpha \cdot t$$

where α represents said rate of change and t represents a time that has elapsed after said radiation dosage calculating means has been reset.

6. An apparatus according to claim 1, wherein said rate of change is calculated as a rate of change of an integrated dose of said radiation, after said radiation dosage calculating means has been reset and until said radiation image starts to be captured by applying said radiation to said subject.

7. An apparatus according to claim 1, wherein said offset value is calculated immediately before said radiation image is captured by applying said radiation to said subject.

8. An apparatus for capturing a radiation image by emitting radiation from a radiation source and applying the radiation to a subject to capture a radiation image thereof, and for controlling said radiation source based on a radiation dosage applied to the subject, comprising:
    dose detecting means for detecting a dose of said radiation applied to said subject;
    radiation dosage calculating means for integrating the detected dose of said radiation with respect to time to calculate a radiation dosage applied to the subject;
    rate-of-change calculating means for calculating a rate of change of a time-integrated output signal from said radiation dosage calculating means before said radiation image is captured by applying said radiation to said subject;
    offset value calculating means for calculating an offset value of said radiation dosage from said rate of change;
    required radiation dosage correcting means for correcting a required dosage of said radiation applied to said subject, based on said offset value; and
    radiation source control means for controlling said radiation source based on the required dosage, as corrected by said required radiation dosage correcting means, and said radiation dosage calculated by said radiation dosage calculating means.

9. An apparatus according to claim 8, wherein said rate-of-change calculating means calculates said rate of change before said radiation is applied.

10. An apparatus according to claim 8, wherein said rate-of-change calculating means calculates said rate of change before said radiation is applied to capture said radiation image and after said radiation is applied to said subject to establish exposure conditions for said radiation source.

11. An apparatus according to claim 8, wherein said rate-of-change calculating means calculates said rate of change dependent on the temperature of said radiation image capturing apparatus.

12. An apparatus according to claim 8, wherein said rate-of-change calculating means calculates said offset value Voff as:

$$Voff = \alpha \cdot t$$

where α represents said rate of change and t represents a time that has elapsed after said, radiation dosage calculating means has been reset.

13. An apparatus according to claim 8, wherein said rate of change is calculated as a rate of change of an integrated dose of said radiation, after said radiation dosage calculating means has been reset and until said radiation image starts to be captured by applying said radiation to said subject.

14. An apparatus according to claim 8, wherein said offset value is calculated immediately before said radiation image is captured by applying said radiation to said subject.

15. A method of capturing a radiation image by emitting radiation from a radiation source and applying the radiation to a subject to capture a radiation image thereof, and for controlling said radiation source based on a radiation dosage applied to the subject, comprising the steps of:
    determining a rate of change over time of an output value from a radiation dosage calculating means for calculating a radiation dosage applied to said subject, before said radiation image is captured by applying said radiation to said subject;
    calculating an offset value of said dosage from said rate of change;
    correcting said radiation dosage calculated by said radiation dosage calculating means based on said offset value when said radiation is applied to said subject; and
    controlling said radiation source based on the corrected radiation dosage to apply the radiation to said subject.

16. A method of capturing a radiation image by emitting radiation from a radiation source and applying the radiation to a subject to capture a radiation image thereof, and for controlling said radiation source based on a radiation dosage applied to the subject, comprising the steps of:
    determining a rate of change over time of an output value from a radiation dosage calculating means for calculating a radiation dosage applied to said subject, before said radiation image is captured by applying said radiation to said subject;

calculating an offset value of said radiation dosage from said rate of change;

correcting a required dosage of the radiation applied to said subject, based on said offset value; and controlling said radiation source based on the corrected required dosage and said radiation dosage calculated by said radiation dosage calculating means to apply the radiation to said subject.

17. An apparatus according to claim 1, wherein the radiation dosage applied to the subject is the total amount of radiation applied to the subject.

18. An apparatus according to claim 1, wherein the rate of change is determined as a function of temperature increase between a start signal and a termination signal of a radiation source.

19. An apparatus according to claim 18, wherein the rate of change is a rate of change of a voltage between the start signal and the termination signal of the radiation source.

* * * * *